US006808930B1

(12) United States Patent
Svanborg et al.

(10) Patent No.: US 6,808,930 B1
(45) Date of Patent: Oct. 26, 2004

(54) THERAPEUTIC AGENTS

(76) Inventors: Catharina Svanborg, University of Lund Department of Laboratory Medicine, Division of Clinical Immunology, Sölvegatan 23, S-223 62 Lund (SE); Per Anders Hakansson, Flormans gatan 2A, S-223 54 Lund (SE)

( * ) Notice: Subject to any disclaimer, the term of this patent is extended or adjusted under 35 U.S.C. 154(b) by 0 days.

(21) Appl. No.: 09/555,270

(22) PCT Filed: Nov. 23, 1998

(86) PCT No.: PCT/IB98/01920

§ 371 (c)(1),
(2), (4) Date: Aug. 30, 2000

(87) PCT Pub. No.: WO99/27967

PCT Pub. Date: Jun. 10, 1999

(30) Foreign Application Priority Data

Nov. 27, 1997 (GB) ............................................. 9725126

(51) Int. Cl.$^7$ .......................... A61K 47/08; A61K 51/08
(52) U.S. Cl. ........................ 436/64; 436/63; 424/130.1; 424/134.1; 424/135.1; 424/178.1; 424/182.1; 424/183.1; 424/1.37; 424/1.53; 424/1.65; 424/1.69; 424/9.1; 424/9.2; 530/365; 530/366; 530/402
(58) Field of Search ................... 436/64, 63; 424/130.1, 424/134.1, 135.1, 178.1, 182.1, 183.1, 1.37, 1.53, 1.65, 1.69, 9.1, 9.2; 530/365, 366, 402, 350; 514/2

(56) References Cited

U.S. PATENT DOCUMENTS

| | | | |
|---|---|---|---|
| 4,348,376 A | * | 9/1982 | Goldenberg |
| 5,614,191 A | * | 3/1997 | Puri et al. |
| 6,455,673 B1 | * | 9/2002 | Collier |

FOREIGN PATENT DOCUMENTS

WO  WO 96/04929  2/1996

OTHER PUBLICATIONS

Blair, A.H. and Ghose, T.I. Linkage of cytotoxic agent to immunoglobulins. Journal of Immunological Methods, 59: 129–143, 1983.*
Johnstone, A. and Thorpe, R. Immunochemistry in Practice, 2$^{nd}$ edition. Blackwell Scientific Publications, Oxford, 1987; pp. 113–130.*
Goers, J. Immunochemical Techniques Laboratory Manual. Academic Press, San Diego, 1993; pp. 69–79.*
Jain, R.K. Barriers to drug delivery in solid tumors.. Scientific American, 271(1): 58–65, 1994.*
Robinett, C.C. et al., Journal of Cell Biology, 135(6): 1685–1700, 1996.*
L.M. Schwartz et al., Immunol. Today 1993, 14:582–590.

D.J. McConkey et al., Mol. Aspects Med. 1996, 17:1–115.
J.F. Kerr et al., Cancer, 1994, 73:2013–26.
M.J. Arends et al., Am. J. Pathol., 1990, 136:593–608.
B. Zhivotovosky et al., FEBS Lett., 1994, 352:150–4.
B. Zhivotovosky et al., Exp. Cell Res., 1995, 221:404–412.
S. Kumar et al, TIBS, 1995, 20:198–202.
L.G. Zheng et al., Nature, 1995, 377:348–351.
W.P. Declercq et al., Cytokine, 1995, 7:701–9.
T.S. Griffith, Science, 1995, 270:1189–1192.
D.A. Jans et al., Physiol Rev, 1996, 76:651–685.
D. Gorlich et al., Science, 1996, 271:1513–1518.
Y. Yoneda, J. Biochem., 1997, 121:811–817.
J. Yang et al., Mol. Cell. Biol, 1994, 14:5088–98 issn 0270–7306.
W.E. Heine et al., J. Nutr., 1991, 121:277–83.
Sheridan et al., Science, 1997, 277:818–821.
Pan et al., Science, 1997, 277:815–818.
S.A. Adam et al., J. Cell Biol., 1990, 111:807–816.
J. Garcia–Bustos et al., Biochim. Biophys. Acta., 1991, 1071:83–101.
J. Ren et al., J. Biol. Chem., 1992, 268:19292–8.
A. Alexandrescu et al., Biochemistry, 1993, 32:1707–1718.
J.J. Kabara et al., Antimicrob. Agents Cehmother, 1972, 2:23–28.
F.D. Gillin et al., Science, 1983, 221:1290–1292.
M.K. Davis et al., Lancet, 1988, ii:365–368.
V. Siskind et al., Am. J. Epidemiol., 1989, 130:229–23.
P.A. Newcomb et all, N. Engl. J. Med., 1994, 330:81–87.
B. Sander et al., Immunol. Rev., 1991, 199:65–92.
J. Graham, Isolation of subcellular organelles and membranes, p. 161–1019 in D. Rickwood, ed., Centrifugation, a practical approach, 2$^{nd}$ ed., IRL Press, Washington, DC.
Hakansson et al, "Multimeric α–Lactalbumin from Human Milk Induces Apoptosis through a Direct Effect on Cell Nuclei", Experimental Cell Res., 246(2):451–460 (1999).
Hakansson et al, "Apoptosis Induced by a Human Milk Protein", Proc. Natl. Acad. Sci. USA, 92(17):8064–8068 (1995).
Li–June Ming, "Two–Dimensional $^1$H NMR Studies of Ca(II)–Binding Site in Proteins Using Paramagnetic Lanthanides (III) as Probes . . . ", Magnetic Resonance in Chem., 31:S104–109 (1993).
Signore et al, "New Approach for In Vivo Detection of Insulitis in Type I Diabetes: Activated Lymphocyte Targeting . . . ", Eur. J. Endocrinol., 131(4):431–437 (1994) Abstract.

* cited by examiner

Primary Examiner—Anthony C. Caputa
Assistant Examiner—Anne L. Holleran
(74) Attorney, Agent, or Firm—Burns, Doane, Swecker & Mathis, L.L.P.

(57) ABSTRACT

An agent comprising a protein complex comprising an oligomeric form of α-lactalbumin (MAL) and a further reagent which is combined with MAL such that it is carried into the nucleoplasm of cells which are susceptible to MAL. Agents of the type, where the further reagent is a therapeutic or labelling reagent, can be used in diagnosis and therapy in particular of cancer.

30 Claims, 11 Drawing Sheets

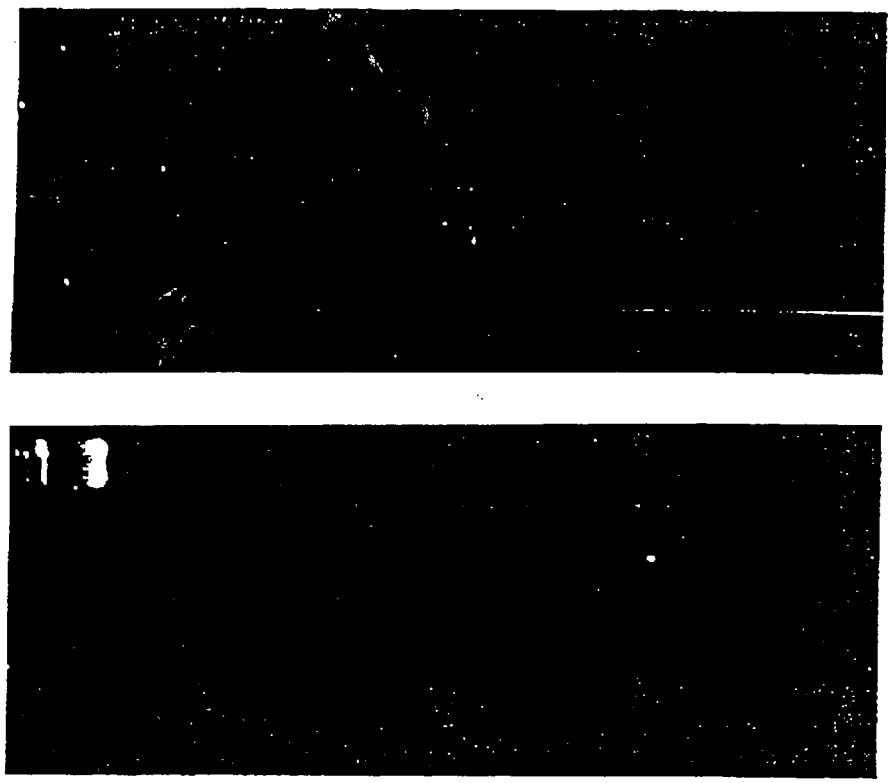
Fig. 1B (II)

THERAPEUTIC AGENTS

CROSS-REFERENCES TO RELATED APPLICATIONS

This application is national stage filing under 35 U.S.C. § 371 of International Application No. PCT/IB98/01920 filed on Nov. 23, 1998, which International Application was published by the International Bureau in English on Jun. 10, 1999, and which claims priority to British Application No. 9725126.8 filed Nov. 27, 1997.

FIELD OF THE INVENTION

The present invention relates to agents which are useful in the diagnosis and treatment of malignancies such as cancer therapy, to processes for their production and to pharmaceutical compositions containing them.

Apoptotic cell death is characterised by loss of cytoplasmic material, nuclear changes with marginalisation of chromatin and by the formation of apoptotic bodies (L. M. Schwartz et al., Immunol. Today 1993, 14:582–590, D. J. McConkey et al. Mol. Aspects Med. (1996) 17:1–115, J. F. Kerr et al., Cancer (1994) 73:2013–26). The reduction in cell viability is accompanied by DNA fragmentation that proceeds in steps with initial formation of high molecular weight (HMW) DNA fragments (50–300 kbp) and the subsequent appearance of oligonucleosome length DNA fragments consisting of oligomers of approximately 200 bp. (M. J. Arends et al., Am. J. Pathol. (1990) 136;593–608, B. Zhivotovosky et al., FEBS Lett. (1994) 352;150–4). Cytoplasmic proteases and $Ca^{2+}$-dependant signaling pathways are activated prior to DNA fragmentation, and are regarded as a prerequisite for the nuclear changes (B. Zhivotovsky et al. Exp. Cell Res. (1995) 221:404–412 m S. Kurar et al., TIBS, (1995) 20:198–202). Agonists like Fas-ligand and TNF first bind to cell surface receptors and then activate transmembrane signaling events that cause cytoplasmic and nuclear changes (L. G. Zheng et al., Nature (1995) 377: 348–351, W. P. Declercq et al, Cytokine (1995, 7:701–9, T. S. Griffith, Science, (1995) 270:1189–1192). Endonuclease activation and DNA fragmentation require that signals from the cytoplasm reach the nucleus. The mechanisms of nuclear uptake and signaling across the nuclear membrane in apoptotic cells remain poorly understood. The transport of macro-molecules from the cytoplasm into the nucleus is highly regulated. Nuclear pore complexes (NPCs) are the sites of exchange of macromolecules between cytoplasm and nucleoplasm (D. A. Jans et al., Physiol. Rev (1996) 76: 651–685, D. Gorlich et al., Science (1996) 271:1513–1518, and Y. Yoneda, J. Biochem. (1997) 121:811–817). The NPCs allow passive diffusion of molecules smaller than 30 kDa but larger proteins like ovalbumin are delayed and bovine serum albumin (66 kDa) does not enter the nucleoplasm. Entry of large molecules or complexes into the nucleus requires active transport and is commonly carrier mediated. The specificity for the carrier may be determined by the so called nuclear targetting or nuclear localization sequences (NLS) that characterize proteins with the ability to enter the nucleus. For example, binding of glucocorticoids to their receptor releases HSP 90 that binds to unoccupied receptors and reveals a NLS in the glucocorticoid receptor sequence that leads to the transport of the glucocorticoid ligand-receptor complex into the nucleus (J. Yang et al., Mol. Cell. Biol. (1994) 14: 5088–98 issn 0270-7306).

A protein complex obtainable from milk that induces apoptosis in tumour cells and immature cells but spares other cells has been described previously (Proc. Natl. Acad. Sci, USA, 92, p8064–8068). The active fraction was initially isolated from human casein by ion-exchange chromatography and was shown by N-terminal amino acid sequencing and mass spectrometry to contain an oligomeric form of α-lactalbumin (described as a multimeric form or "MAL"). Monomeric α-lactalbumin is the major protein component in human milk whey, where it occurs at concentrations around 2 mg/ml (W. E. Heine et al., J. Nutr. (1991) 121: 277–83), but monomeric α-lactalbumin isolated from human whey did not induce apoptosis. Further analysis has provided evidence that the apoptosis-inducing fractions contains oligomeric forms of α-lactalbumin with structural properties distinct from monomeric α-lactalbumin as it occurs in whey. The apoptosis inducing fraction is referred to hereinafter as MAL. It is possible that the mechanism by which the oligomer induces apopotosis may relate to the $Ca^{2+}$ binding properties of MAL since apoptosis required extracellular calcium.

MAL may be derived from other sources of α-lactalbumin such as bovine, sheep or goats milk or human whey.

It has now been found that MAL is taken up by susceptable cells (i.e. tumour cells) and accumulated in cell nuclei. This high uptake by the nucleus, combined with its oligomeric protein structure, means that MAL would provide a useful carrier for other moieties for example, cytotoxins or chemotherapeutic agents whose effect would supplement the a effect of MAL in killing tumour cells, or diagnostic reagents such as dyes or radio- or other labels which would allow identification of tumour cells, whilst at the same time, allowing MAL to exert a killing effect on those cells.

SUMMARY OF THE INVENTION

The present invention provides an agent comprising a protein complex comprising an oligomeric form of α-lactalbumin (MAL) and a further reagent which is combined with MAL such that it is carried into the nucleoplasm of cells which are susceptible to MAL.

The said further reagent may be coupled by conjugation or by covalent bonding for example by way of a linking or spacer group as would be understood in the art. Enzymatic reactions can mediate or facilitate the coupling.

Recombinant production techniques allows also the possiblity that MAL could be produced in the form of a fusion protein with the said further reagent.

Examples of said further reagents include cytoxins such as known chemotherapeutic reagents used for the treatment of cancer, microbial toxins such as diptheria toxin and monoclonal antibodies. Alternatively, the said further reagent comprises a labelling agent such as biotin or radioactive labels such as $^{125}I$. For example, a labelling group can be introduced into a protein using an enzymatic reaction or by having a labelled building stone (such as radioactive isotopes e.g. $^{14}C$, $^{35}S$,) within the protein. $^{125}I$-labelling can be performed enzymatically by coupling $^{125}I$ to the protein with the help of lactoperoxidase. Biotinylation of the protein is performed by letteing D-biotinoyl-ϵ-aminocaproic acid-N-hydroxysuccinimide ester react with the protein by forming a stable amide bond to free amino groups in the protein.

Protein may also be labelled by adding radioactive amino acid during the production of a recombinantly produced protein.

Depending upon the nature of the said further reagent, the complex of the invention can be used in the diagnosis and/or treatment of cancer. For this purpose, the complex is suitably formulated as a pharmaceutical composition and these form a further aspect of the invention.

The complex can be administered in the form of an oral mucosal dosage unit, an injectable composition, or a topical composition. In any case the protein is-normally administered together with the commonly known carriers, fillers and/or expedients, which are pharmaceutically acceptable.

In case the protein is administered in the form of a solution or cream for topical use the solution contains an emulsifying agent for the protein complex together with a diluent or cream base. Such formulations can be applied directly to the tumour, or can be inhaled in the form of a mist into the upper respiratory airways.

In oral use the protein is normally administered together with a carrier, which may be a solid, semi-solid or liquid diluent or a capsule. Usually the amount of active compound is between 0.1 to 99% by weight of the preparation, preferably between 0.5 to 20% by weight in preparations for injection and between 2 and 50% by weight in preparations for oral administration.

In pharmaceutical preparations containing complex in the form of dosage units for oral administration the compound may be mixed with a solid, pulverulent carrier, as e.g. with lactose, saccharose, sorbitol, mannitol, starch, such as potato starch, corn starch, amylopectin, cellulose derivatives or gelatine, as well as with an antifriction agent, such as magnesium stearate, calcium stearate, polyethylene glycol waxes or the like, and be pressed into tablets. Multiple-unit-dosage granules can be prepared as well. Tablets and granules of the above cores can be coated with concentrated solutions of sugar, etc. The cores can also be coated with polymers which change the dissolution rate in the gastrointestinal tract, such as anionic polymers having a $pk_a$ of above 5.5. Such polymers are hydroxypropylmethyl cellulose phthalate, cellulose acetate phthalate, and polymers sold under the trade mark Eudragit S100 and L100.

In preparation of gelatine capsules these can be soft or hard. In the former case the active compound is mixed with oil, and the latter case the multiple-unit-dosage granules are filled therein.

Liquid preparations for oral administration can be present in the form of syrups or suspensions, e.g., solutions containing from about 0.2% by weight to about 20% by weight of the active compound disclosed, and glycerol and propylene glycol. If desired, such preparations can contain colouring agents, flavouring agents, saccharine, and carboxymethyl cellulose as a thickening agent.

The daily dose of the active compound varies and is dependant on the type of administrative route, but as a general rule it is 1 to 100 mg/dose of active compound at personal administration, and 2 to 200 mg/dose in topical administration. The number of applications per 24 hours depend of the administration route, but may vary, e.g. in the case of a topical application in the nose from 3 to 8 times per 24 hours, i.e., depending on the flow of phlegm produced by the body treated in therapeutic use.

The invention further provides a method for treating cancer which comprises administering to cancer cells a complex or a composition as described above.

Diagnostic applications of the complex of the invention may be carried out in vivo or in vitro for example on biopsy samples. For this purpose, a complex comprising a label may be applied to the suspect tumour in the form of a pharmaceutical composition when used in vivo or any formulation when used in vitro. The tumour can then be observed in order to determine whether the complex penetrates into the nucleus or not. Visibility of the nucleus would be indicative that the complex has been absorbed into the nucleus and is a MAL susceptible tumour. Although the degree of uptake of MAL is variable, it is taken up by cancer cells generally and therefore may be used in killing those cells, particularly when combined with another cellular toxin in a complex of the invention. Uptake of MAL is particularly high in lymphoid tumour cells such as leukaemia cells. Even in carcinoma cells such as lung cancer cells, there is sufficient uptake to result in cell death as will be illustrated hereinafter. The information obtained using diagnostic methods of the invention may assist in determining a future treatment regime.

The interaction of MAL with different cellular components was studied by confocal microscopy, using biotinylated MAL, and by subcellular factionation using $^{125}$I-labelled MAL. Monomeric α-lactalbumin and human IgG were used as controls. MAL was found to accumulate in cell nuclei rather than the cytosol, the vesicular fraction or the ER-Golgi complex. The nuclear accumulation of MAL occurred rapidly in cells that were susceptible to its apoptosis-inducing effects, but not in resistant cells. Nuclear uptake was through the nuclear pore complex and was critical for the induction of apoptosis, since inhibition of nuclear uptake with WGA rescued digitonin-permeabilized cells from apoptosis. $Ca^{2+}$ was required for MAL induced DNA fragmentation but nuclear uptake of MAL was independent of $Ca^{2+}$.

The results demonstrated that MAL can target cell nuclei and that nuclear targeting mechanisms are more readily available in cells that are sensitive to MAL-induced apoptosis than in resistant cells. It appears that apoptosis induction occurs at least in part through a direct effect of MAL at the nuclear level.

Cell surface binding of MAL as a possible decisive step in apoptosis induction was investigated first. Exogenous apoptosis-inducing molecules like Fas-ligand or TNF bind to their respective cell surface receptors and trigger transmembrane signalling event and intracellular pathways leading to apoptosis. MAL bound quickly to cell surfaces, was saturate at high MAL concentrations and was specific as defined by competition experiments where labelled MAL was competed out by unlabeled MAL. By confocal microscopy MAL was ,shown to bind in patches, suggested that either MAL bound as preformed aggregates, or that the bound MAL accumulated in certain areas of the membrane through capping or other mechanisms influencing receptor distribution. There was little quantitative difference in cell surface binding of monomeric, inactive and oligomeric, active forms of the protein. Furthermore, there was no difference in cell surface binding to sensitive and resistant cells. The results suggested that MAL differs from agonists like TNF and Fas-ligand in that cell surface binding does not itself trigger apoptosis. Recently Sheridan et al. (Science, (1997) 277:818–821 and Pan et al. (Science (19970 277:815–818) described a decoy receptor lacking the signalling domain of the native receptor, in the membrane of healthy cells [Pan, 1997 #640,; Sheridan, 1997 #639]. The TRAIL protein binds cell surface receptors with similar affinity, but will not be able to induce an apoptosis-signal in healthy cells.

MAL was rapidly taken into the nuclei of cells that were sensitive to its apoptosis inducing effect, suggesting that it was capable of nuclear targeting. This term is used herein to describe preferential localisation of certain molecules to the nuclear compartment. Molecules of diverse origin, structure and function share the ability to reach cell nuclei, and may exert their main functions there as opposed to the cytoplasmic compartment. The uptake of MAL into the nucleus was via the nuclear pore complex as shown by inhibition studies using WGA, a lectin that binds to glycosylated regions of the nucleoporins and sterically hinders transport of the importin-protein complex through the nuclear pore (S. A. Adam et al., (1990) J. Cell Biol. 111:807–816). WGA treatment blocked MAL uptake into the nuclei of digitonin-treated cells and inhibited the MAL-induced DNA fragmentation. The structural basis for and mechanism of nuclear uptake of MAL need to be identified. Classical nuclear targeting sequences often include clusters of basic amino acids, that share little or no sequence homology (Jans et al. (1996) supra., J. Garcia-Bustos et al., Biochim Biophys. Acta. (1991) 1071: 83–101). Sequence analysis of the monomeric form of α-lactalbumin did not show the presence of known nuclear targeting motifs and the monomer did not target cell nuclei. It is likely, therefore that MAL carried structural modifications that confer affinity for the nuclear compartment, the nuclear membrane and/or the nuclear pore.

The susceptibility to MAL-induced apoptosis in difference cells was proportional to the nuclear accumulation of MAL. MAL rapidly entered the nuclei of the sensitive L1210 cells. At a concentration of 0.3 mg/ml nuclear staining was observed after 1 hour in 10% of cells and increased to 75% after 6 hours. DNA fragmentation was first seen after 6 hours incubation. Nuclear uptake occurred more slowly in the intermediary sensitive A549 cell line and was low or absent in human kidney cells.

The difference was not observed when the total, cell-associated MAL or cytoplasmic uptake of MAL was compared between the cells. Uptake into the cytoplasm occurred with similar kinetics in the L1210, A549 and HRTEC cells. The total amount of intracellular MAL was highest in the L1210 cells but most of this was in the nuclei and not in the cytoplasm. This suggested that the nuclear uptake was the decisive step. Further evidence for a direct effect of MAL at the nuclear level was obtained using isolated nuclei. MAL induced DNA fragmentation in isolated nuclei at concentrations lower than those required for whole cells. It should be noted that isolated nuclei from the three cell types were all susceptible to the effects of MAL and showed similar kinetics of DNA fragmentation. (HMW-oligonucleosome length fragments. Differences between intact nuclei and isolated nuclei). These results suggested that the decisive event separating sensitive from resistant cells was the actual transport of MAL from the cytoplasm into the nuclei, rather than the effect of MAL once in the nuclear compartment.

Lactalbumins are $Ca^{2+}$ binding proteins with one high affinity and one low affinity $Ca^{2+}$ binding site (J. Ren et al., J. Biol. Chem. (1992) 268;19292–8). MAL induced apoptosis was previously shown to require extracellular $Ca^{2+}$ (A. Hikansson et al., (1995) supra.). In this study, the applicants examined the effect on nuclear targeting and on DNA fragmentation of various agents that alter extra- or intracellular $Ca^{2+}$ levels. Pre-treatment of sensitive cells with $Ca^{2+}$-chelators was found to inhibit MAL-induced DNA fragmentation in isolated nuclei. There was however no effect on the nuclear targetting process. These observations suggested that apoptosis occurs as a result of two converging mechanisms; the transport of MAL to the nucleus and changes in the available $Ca^{2+}$ concentration.

Therefore, when applying the treatment of the invention for example by using a pharmaceutical composition, care should be taken that the calcium levels are sufficient to ensure that cells can be killed. However high calcium levels can lead to inactivation of MAL. Therefore, the inclusion of calcium agents in the formulation should be avoided.

MAL contains as its major constituent oligomers of α-lactalbumin. The α-lactalbumin protein family has been extensively studied and characterised at the molecular level. Lactalbumins from different species show little structural variation, but the amounts are higher in e.g. human compared with bovine milk. The monomeric form of α-lactalbumin has a molecular mass of 14 kDa and is the quantitatively dominating whey protein in human milk (W. E. Heine et al., (1991)supra.). MAL, on the other hand, was not derived from whey but from casein fraction of human milk after precipitation at low pH. The active fraction bound with high affinity to an ion-exchange matrix, eluted with high salt and was found to contain several oligomeric forms of α-lactalbumin. Low pH and variable anionic conditions have previously been shown to alter the molecular structure of monomeric α-lactalbumin to the so-called molten globule state, Molten globules are partially unfolded intermediates between the native and fully denatured forms of α-lactalbumin (K. Kuwajima., Faseb J. (1996) 10:102–109, A. Alexandrescu et al., Biochemistry (1993) 32: 1707–1718). Preliminary results from structural studies suggest that MAL contains partly refolded oligomers with structural features distinct from the monomeric α-lactalbumin as it occurs in human whey.

Additionally MAL often contains lipids and in particular MAL derived from human milk contains phospholipids, monoglycerides, diglycerides, cholesterol, triglycerides and free fatty acids. Specifically the free fatty acid content of MAL appears to be higher than that found in fresh milk. The role of these lipids in apoptosis or in the stabilisation of the MAL structure is not fully clear. However, the presence of these components in MAL is preferred for its therapeutic effect.

This study confirmed the difference in apoptosis inducing activity between MAL and monomeric α-lactalbumin, and showed distinct difference in their cellular interactions. Monomeric α-lactalbumin bound to cell surfaces and entered the cytoplasm, but did not accumulate in cell nuclei. There was no effect of α-lactalbumin at the nuclear level even in digitonin-permeabilized cells, when the protein was allowed to diffuse freely into the nuclei. Furthermore, these was no difference in subcellular distribution of the monomer between apoptosis sensitive and resistant cells. The results demonstrate that structural modifications or additional milk constituents present in MAL are required for nuclear targeting and induction of apoptosis.

Human milk provides the breast-fed infant with a mucosal immune system. Molecules in milk prevent microbial attachment to mucosal tissues, lyse viral particles, disrupt bacterial cell walls and prevent microbial growth (H. McKenzie et al., Adv. Protein Chem., (1994) 44: 173–313, J. J Kabara et al., Antimicrob. Agents Chemother (1972) 2:23–28, F. D. Gillin et al., Science (1983) 221: 1290–1292). Epidemiological studies consistently find lower frequencies of viral and bacterial infections in breast-fed infants. Epidemiological studies have also provided compelling evidence that breast30 feeding may protect against cancer. Breast-fed individuals have a lower incidence of lymphomas and other malignancies, and the frequency decreases with the length of breast-feeding (M. K. Davis et al., Lancet (1988) ii: 365–368). There are other reports to suggest that the breast cancer incidence is reduced in women who breast-feed their children (V. Siskind et al., Am. J. Epidemiol. (1989) 130: 229–236, P. A. Newcomb et al., N. Engl. J. Med. (1994) 330: 81–87) Our studies provide a potential mechanism for the reduced disease frequencies. MAL may reach the rapidly proliferating cells in the gut of the breast-fed infant and drive selection through maturity and away from the neoplasia or reach the mucosa-associated lymphoid tissue and influence the function of local lymphocyte populations.

Figure 2A:
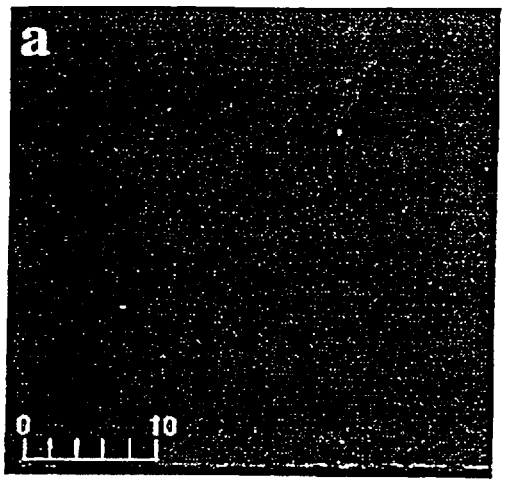
Figure 2A:
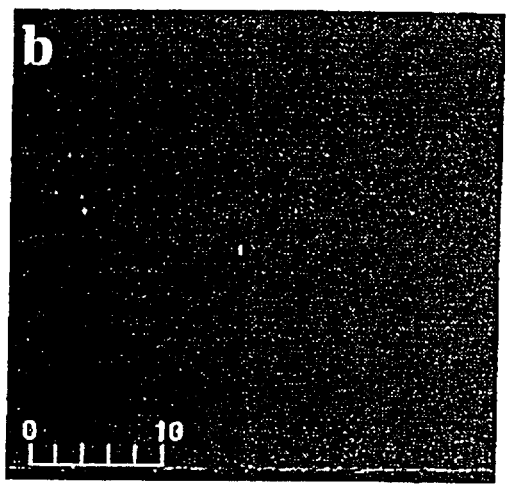
Figure 2A:
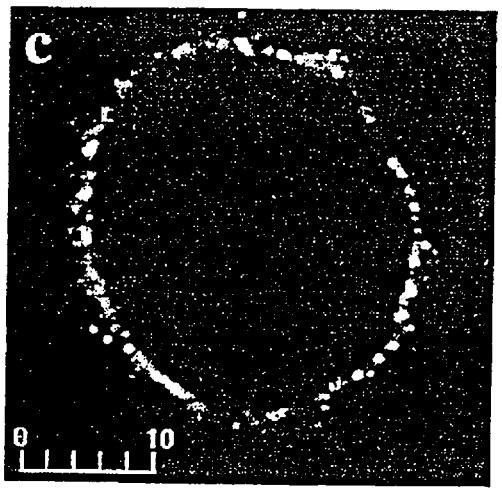
Figure 2A:
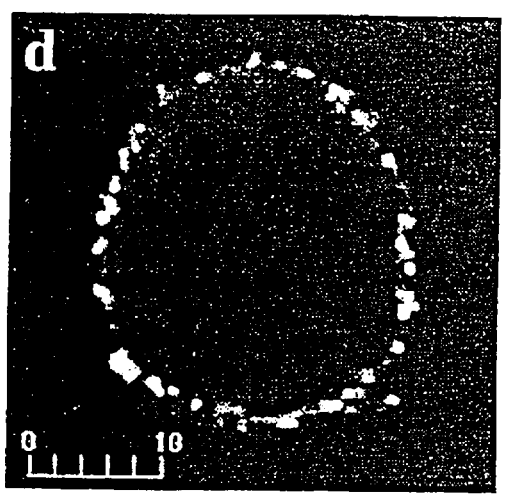
Figure 2B:
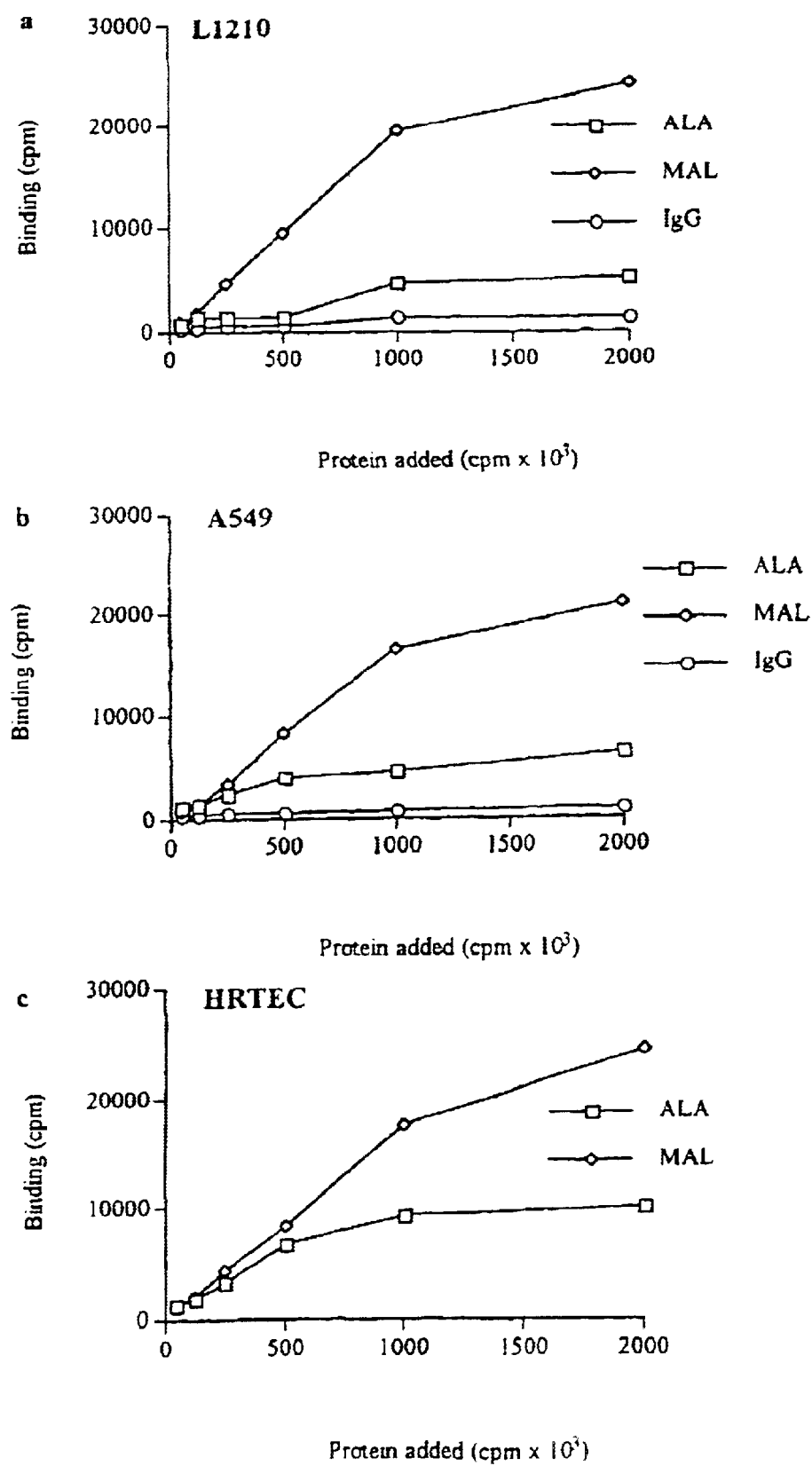

The cells were incubated with the concentration of MAL killing 50% of the cells ($LD_{50}$ concentration) after 6 h (L1210) or 24 h (A549 and HRTEC cells). The LD50 concentration for the different cells was 0.5 mg/ml for L1210 cells, 1.25 mg/ml for A549 cells and 4.5 mg/ml for HRTEC cells;

FIG. 2A shows the cell surface binding of biotinylated MAL (d) and α-lactalbumin (c) with streptavidin (a) and Ig G (b) as controls as visualised by confocal microscopy;

FIG. 2B shows the cell associated radioactivity in L1210, A549 and HRTEC cells after 30 min exposure to increasing concentrations of radiolabeled MAL (-▣-), ALA (-□-) or IgG (-O-).

Figure 3:
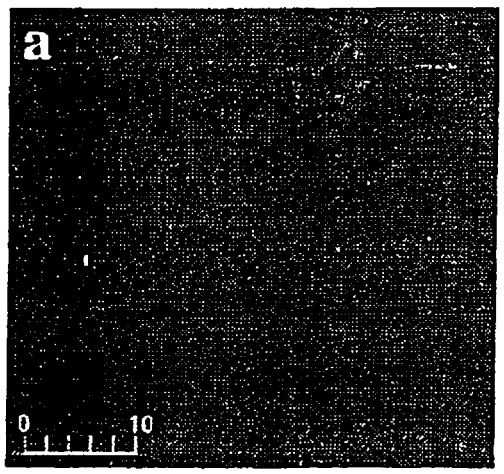
Figure 3:
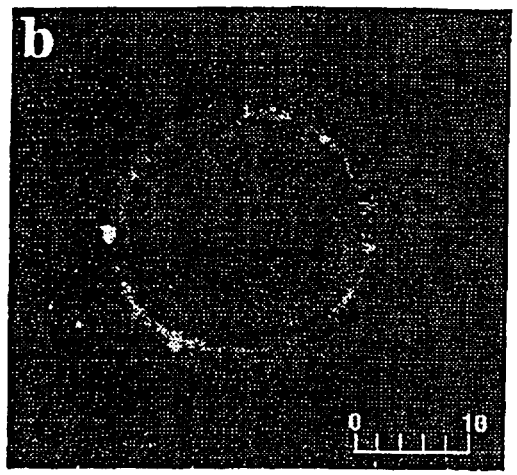
Figure 3:
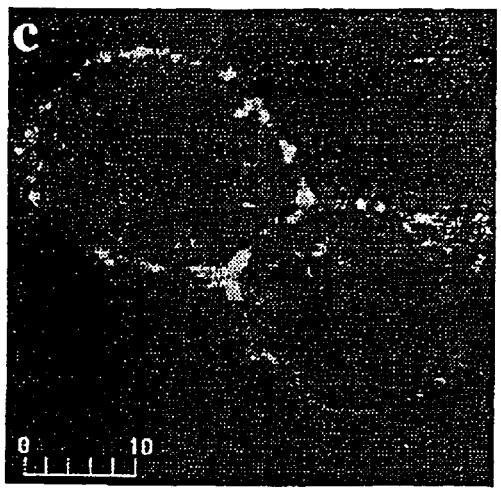
Figure 3:
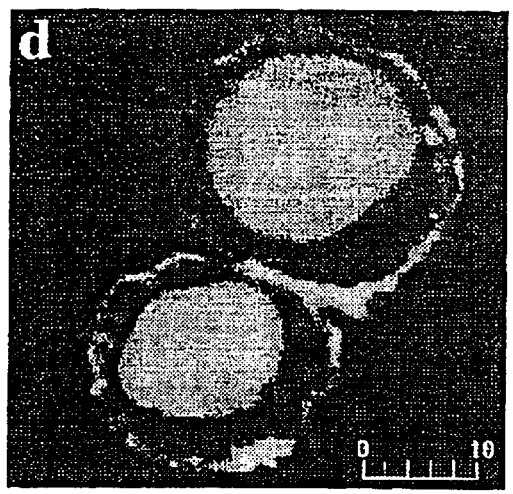
Figure 4:
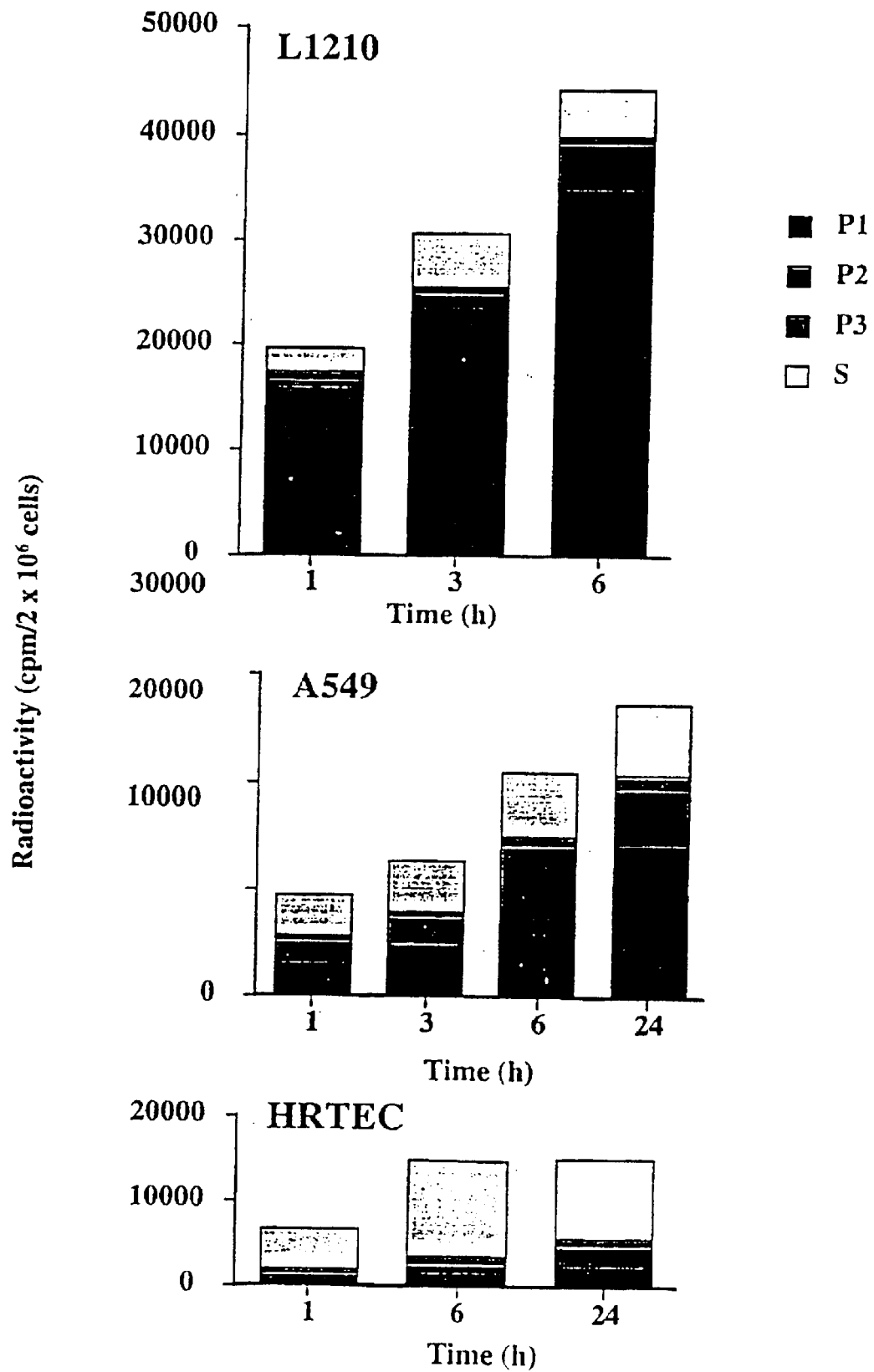
Figure 5:
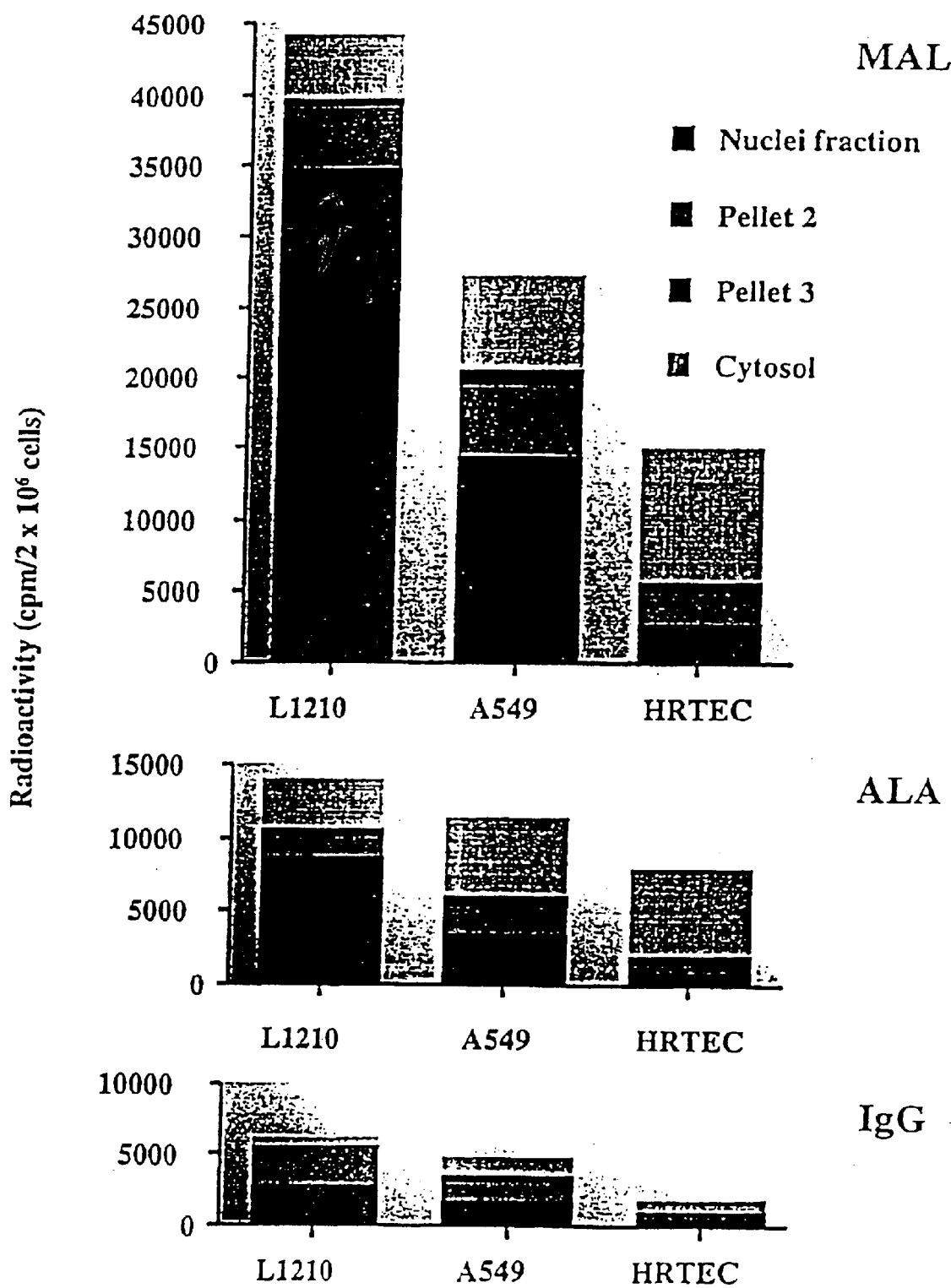

FIG. 3 shows interaction of MAL with different cellular compartments in A549 cells. (a) Streptavidin control. (b) Cell surface binding detected after 30 min incubation. The morphology and intensity of MAL cell surface binding was similar for the three cell types, and for ALA. (c) Cytoplasmic, granular fluorescence was detected after 3 h incubation with MAL. (d) Nuclear accumulation was maximal after 24 h incubation. The nuclear accumulation was more rapid in the L1210 cells. Nuclear accumulation of MAL was not observed in the HRTEC cells. The scale bar units are in μm;

FIG. 4 shows localization of $^{125}$I-labeled MAL to different subcellular compartments in L1210, A549 and HRTEC cells. Cells were exposed to $10^6$ cpm of radiolabeled KM., homogenized, and radioactivity associated with each subcellular fraction was quantitated in a γ-counter. The nuclear fraction contained mostly nuclei, pellet 2 contained plasma-, Golgi-, ER-membranes and mitochondria, pellet 3 contained small vesicles and the supernatant contained the cytosol;

FIG. 5 illustrates difference in subcellular distribution between MAL and ALA. L1210, A549 and HRTEC cells were exposed to $10^6$ cpm of radiolabeled proteins for 6 h, 24 h and 24 h, respectively. The cells were homogenized, subjected to differential centrifugation and the radioactivity of each subcellular fraction was determined.

Figure 6:
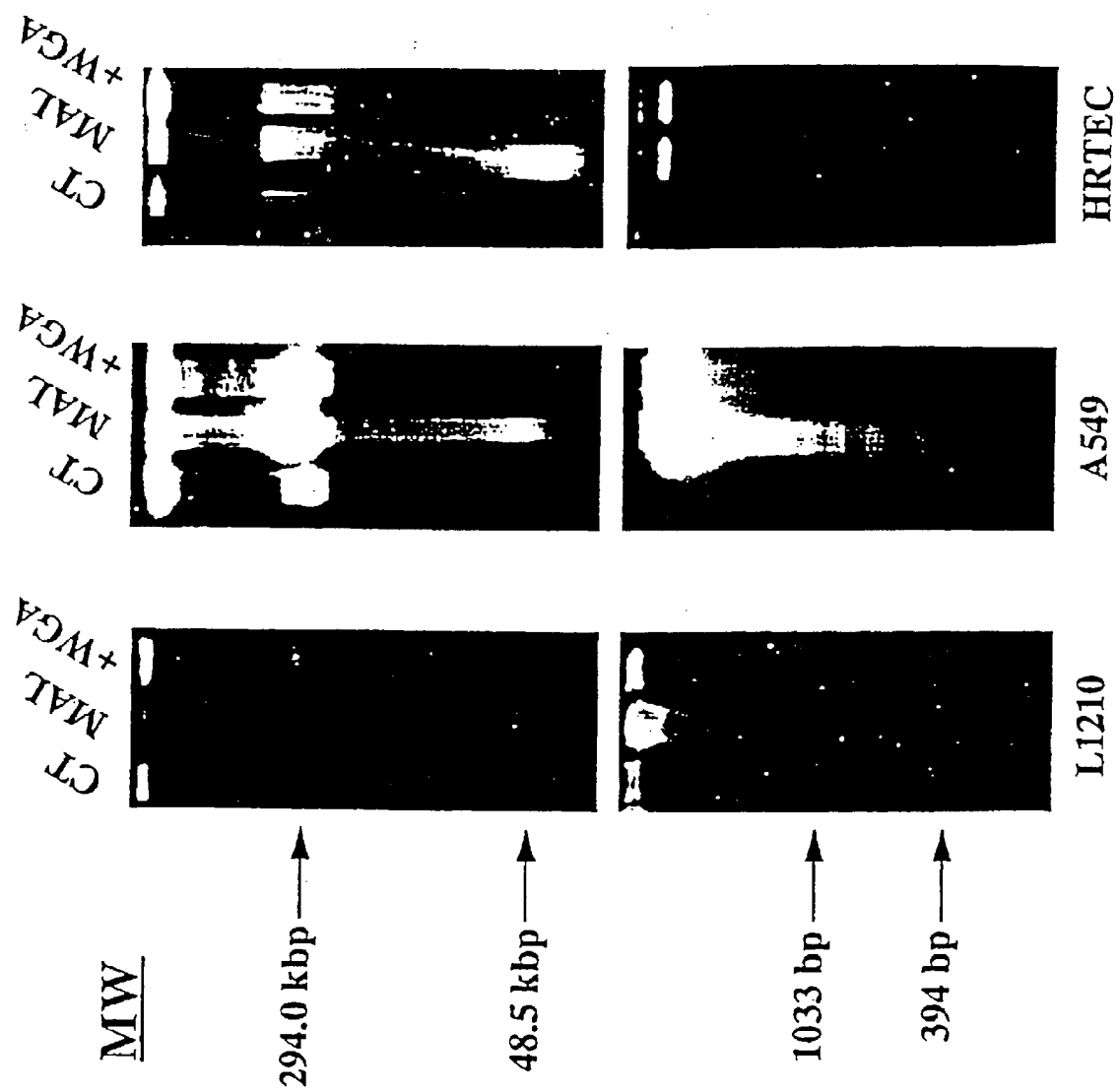
Figure 7:
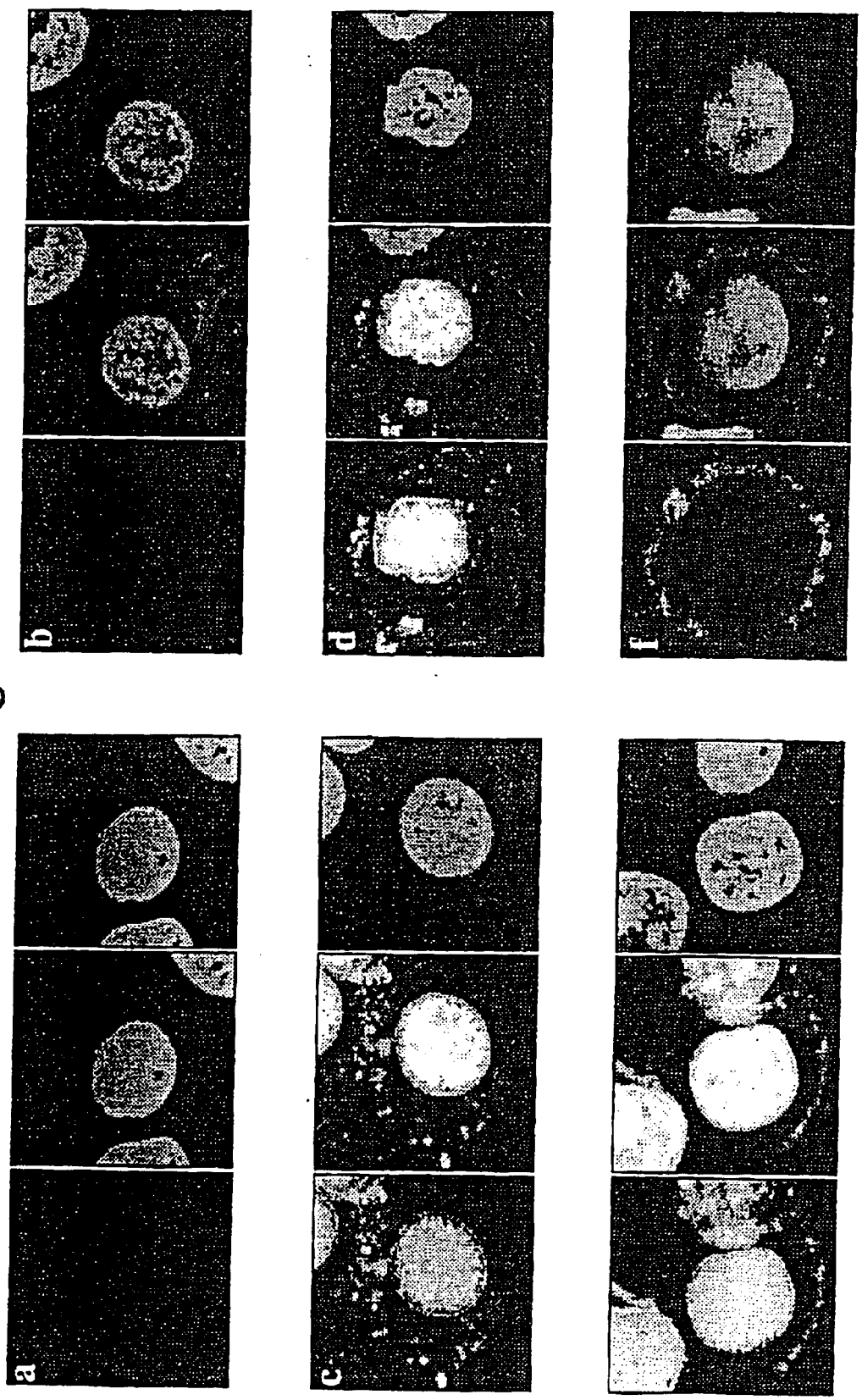
Figure 8:
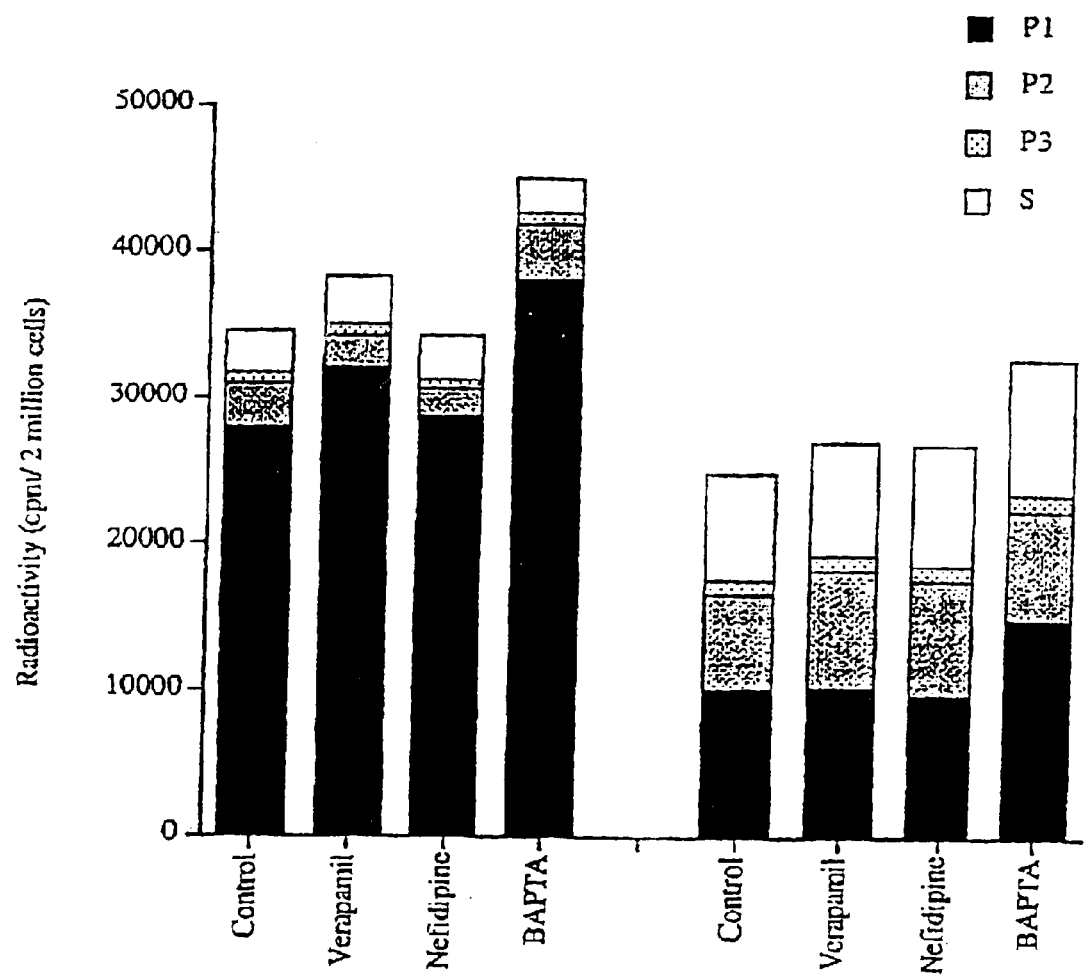

FIG. 6 illustrates the chromatin cleavage induced by MAL in L1210, A549 and HRTEC nuclei after 2 hours incubation with 0.4 mg/ml of MAL. For inhibition experiments, the isolated nuclei were preincubated with 50 μg/ml of WGA before the addition of protein. Chromatin cleavage was analysed by field-inverse gel electrophoresis (top) and oligonucleosomal fragmentation was detected by conventional gel electrophoresis (bottom);

FIG. 7 shows nuclear uptake of MAL, ALA and IgG into the nuclei of digitonin-permeabilized A549 cells. Digitonin—permeablized cells were incubated with biotinylated protein for 20 minutes, washed, counterstained with FITC-conjugated strepavidin (green colour) and visualised by confocal microscopy. Nuclear DNA was counterstained with 25 μg/ml of propidium iodide (red colour). Nuclear staining is shown for cells exposed to streptavidin alone (a) IgG (b) ALA (c and d) and MAL (e and f). For inhibition experiments the digitonin-permeabilized cells were preincubated with 50 μg/ml of WGA before the addition of biotinylated protein. Nuclear uptake of MAL was inhibited with WGA (f), but ALA was still taken up (d); and FIG. 8 shows the effect of subcellular distribution of MAL after treatment with $Ca^{2+}$ inhibitors. L1210 and A549 cells were pretreated with 0.5 mM BAPTA/AM, 10 μM verapimil or 5 μM nefidipine before exposure to $10^6$ cpm of radiolabelled proteins for 6 hours and 24 hours respectively. The cells were homogenized, subjected to differential centrifugation and the radioactivity of each subcellular fraction was determined.

DETAILED DESCRIPTION OF THE INVENTION

In the examples, the following reagents were used:

FITC conjugated swine anti-rabbit antibodies, and FITC conjugated streptavidin were from Dakopatts a/s (Glostrup, Denmark). DEAE-Trisacryl M was from BioSepra (Villeneuve la Garenne, France). The Biotin Labelling kit was from Boeringer Manheimer GmbH (Germany) and $^{125}$I was from Amersham (UK). Flowcheck™ and Flowser™ fluorospheres were from Coulter Inc. (Hialeah, Fla., USA). Seaplaque GTG Low melting temperature agarose gel and SeaKem GTG agarose were from SeaKem, FMK Bioproducts (Rockdale, USA). Dulbecco's modified Eagle's medium, Hank's balanced salt solution (HBSS), RPMI 1640, fetal calf serum (FCS), L-glutamine, 2-mercaptoethanol, penicillin, streptomycin, gentamicin and I kD DNA ladder was from Gibco/BRL, Life Technology Ltd (Paisley Scotland, UK). Boric acid, dimethylsulfoxide, $Na_2HPO_4$, NaCl, $KH_2PO_4$, $MgCl_2$, NaAzid, Tween-20 and tris(hydroxymethyl) aminomethane was from Kebo Lab (Stockholm, Sweden). The PD-10 column, heparin and percoll solutions were from Pharmacia Biotech (Stockholm, Sweden), α-lactalbumin, leupeptin, antipain, PMSF, Triton X-100, NP-40, CHAPS, trypsin, butyrate, N-lauroylsarcosine, sodium periodate, proteinase K, tunicamycin, lactoperoxidase, EDTA, EGTA, collagenase type I, DNAse type IV and two sets of pulse markers: chromosomes from Saccharomyces cerevisiae (225–2200 kbp) and a mixture of λDNA Hind III fragments, λDNA and λDNA concatemers (0.1–200 kbp) were from Sigma Chemicals Inc (St Louis, USA).

The murine lymphoblastoid leukemia cell line L1210 (ATCC CLL 219) was cultured in in RPMI 1640 supplemented with 10% FCS, 2 mM glutamine and 50 μg of gentamicin per ml with the addition of 50 μM 2-mercaptoethanol. Cells were aspirated from the flasks, harvested by centrifugation, washed and resuspended in RPMI.

The human lung carcinoma cell line A549 (ATCC CLL 185) was cultured as described above but without 2-mercaptoethanol in the medium. The cells were detached by versene (0.2 g Sodium EDTA per liter PBS) for about 10 min at 37° C. Detached cells were harvested by centrifugation at 320×g for 10 min and resuspended in RPMI.

Human renal tubular epithelial cells (HRTEC) were isolated from the kidney of a three year old boy whose kidney was removed due to hydronephrosis and reduced function. Renal cotex was dissected from renal medulla, minced and collected by centrifugationat 250×g for 10 min. The cortical fragments were incubated overnight at 4° C. on a rotational platform in phosphate buffered saline (PBS) 0.15M pH7.2 containing 0.1% collagenase type I (Sigma) and 0.04% DNAse type IV (Sigma). Tissue was collected by centrifugation (250×g for 10 min) and diluted in an equal volume HBSS, supplemented with 15% fetal calf serum. The tissue was resuspended in eight volumes of HBSS with 15% FCS, applied to the top of a two step Percoll gradient: 30 and 50% diluted in HBSS, centrifuged at 1500×g for 20 min at 4° C. and the interface collected. This interface was diluted in four volumes of HBSS with 15% FCS, centrifuged at 250×g for 10 min and resuspended in Primaria flasks in Dulbecco's modified Eagle's medium supplemented with 15% FCS, 2 mM L-glutamine, 20 units/ml heparin, 100 U/ml of penicillin and 100 µg/ml streptomycin. Cells were incubated at 37° C. in an atmosphere of 95% air and 5% $C_{O2}$ and grown to confluence. After trypsinization the cell suspension was filtered through a 35 µm nylon mesh, replated in Primaria flasks and grown to confluence. The cell isolates were trypsinized, concentrated in FCS containing 5% DMSO and stored in liquid nitrogen for subsequent use. Cells used in experiments were passaged 3–4 times and cultured as above for A549 cells.

MAL was purified from frozen milk as described for example in WO 96/04929. Briefly, human milk was thawed and centrifuged to remove fat. The defatted milk was separated into casein and whey by acid precipitation (O. Melander, 1947, Uppsala Lkarfören, Förhandl. 3–4: 107–198). The casein precipitate was harvested by centrifugation, washed by 3–5 cycles of resuspension in distilled water and lyophilised. The casein was fractionated using an ion-exchange column packed with DEAE-Trisacryl M attached to an FPLC instrument (Pharmacia-LKB, Uppsala, Sweden) with a NaCl gradient. The MAL complex eluted with 1 M NaCl. The eluant was desalted by dialysis (membrane cut off 3.5 kD) against distilled water for at least 48 h, lyophilised and resuspended to appropriate concentrations.

EXAMPLE 1

Susceptability of Cells to MAL-induced Apoptosis

L1210, A549 and HRTEC cells were resuspended in RPMI ($2 \times 10^6$ cells/ml). The cell suspension (900 µl) was mixed with MAL (100 µl) in a 24-well plate incubated for 6 h or 24 h respectively, at 37° C. and harvested by aspiration. Cell aliquots were tested for viability by trypan blue exclusion. Remaining cells were analysed for DNA fragmentation.

DNA fragmentation was detected by agarose gel electrophoresis (HAkansson et al. (1995)supra.). Briefly, cells ($2 \times 10^6$) were suspended in 250 µl of TE-buffer (10 mM Tris, 1 mM EDTA, pH 8.0) and 250µ of ice-cold lysis buffer (0.5% Triton X-100, 5 mM Tris, 20 mM EDTA, pH 8.0), vortexed and allowed to lyse on ice for 1 h. DNA fragments were separated from intact chromatin by centrifugation at 13,000×g for 15 min. The supernatant was transferred to new tubes and DNA was precipitated at −20° C. after addition of 1 ml cold, absolute ethanol and 25 µl of 5M NaCl. Precipitated DNA was pelleted by centrifugation at 13,000×g for 15 min and dried in a Speed-Vac Concentrator (Savant Instruments Inc., Farmingdale, N.Y., USA) until ethanol had vaporised. The pellet was resuspended in 30 µl of TE-buffer and incubated for 1 h at 37° C. with 1 mg/ml of RNAse A followed by 1 h with 500 µg/ml of Proteinase K. Samples-were loaded on 1.8% agarose gels, and run overnight applying a 40 V constant voltage. DNA was visualised under ultraviolet light (305 nm) after straining with ethidium bromide (6 µg/ml) and photographed using Polaroid 55 positive-negative film. DNA size was calibrated using 1 kD DNA ladder (Gibco BRL, Life Technologies LTD., Paisley, UK), consisting of 1018 bp dsDNA fragment repeats and vector DNA ranging from 75–1636 bp.

High molecular weight DNA fragments were detected by field-inversion gel electrophoresis (FIGE). Briefly, cells ($2 \times 10^6$) were suspended in 180 µg of buffer (0.15 M NaClaniacal, 2 mM $KH_2PO_4$/KOH, pH 6.8, 1 mM EGTA, 5 mM $MgCl_2$) and 180 µl of 37° C. molten 1% low melting point agarose gel (SeaKem, FMK Bioproducts, Rockdale, USA) and pipetted into plugs at precoled plates and left for 10 min at 4° C. The plugs were incubated in 1 ml/plug of incubation buffer (10 mM NaCl, 10 mM Tris, pH 9.5, 25 mM EDTA, 1% N-lauroylsarcosine, supplemented with proteinase K at a final concentration of 0.2 mg/ml) at 50° C. for 24 h. The incubation was followed by rinsing in 3 changes of TE-buffer at 4° C. for 2 h. The plugs were stored in 50 mM EDTA until run. Electrophoresis were run at 180 V in 1% agarose gels in 0.5×TBE (45 MM Tris, 1.25 mM EDTA, 45 mM boric acid, pH 8.0), at 12° C., with the ramping rate changing from 0.8 s to 30 s for 24 h, using a forward to reverse ratio of 3:1. DNA size calibration was performed using two sets of pulse markers: chromosomes from Saccharomyces cerevisiae (225–2200 kbp) and a mixture of XDNA and XDNA concatemers (0.1–200 kbp) purchased from Sigma. Gel staining and photography were performed as described above.

Figure 1A:
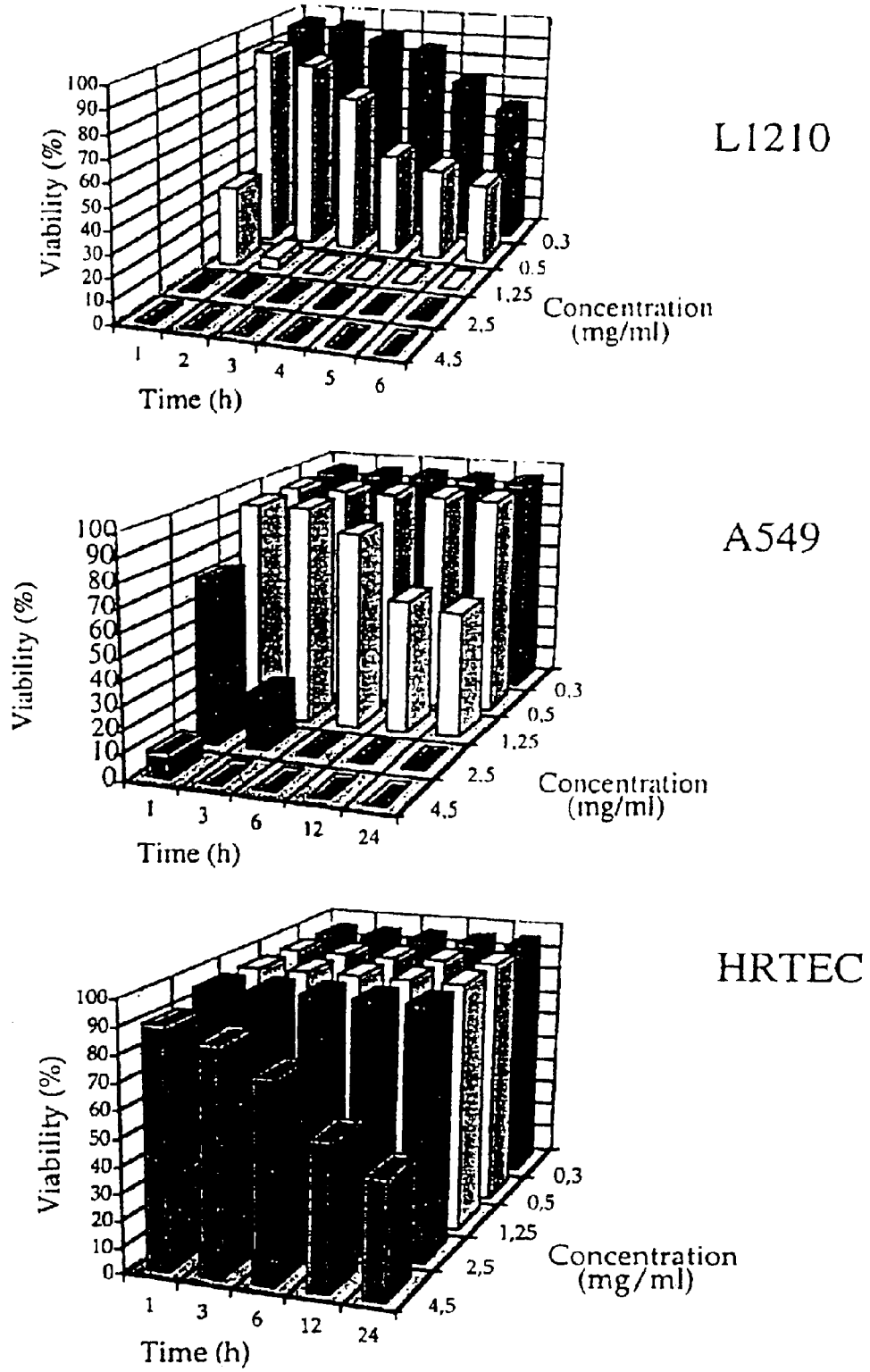
FIG. 1A shows the results of viability studies on the incubation of three cell types with different concentrations of MAL incubated for different lengths of time. The viability was determined by trypan blue exclusion as of cells exposed to medium alone.

The L1210 cells died when exposed to 0.5 mg/ml of MAL, with 50% of the cells remaining viable after 6 h (FIG. 1A). The A549 cells required a higher concentration (1.25 mg/ml of MAL) and a longer incubation time (24 hours) in order for 50% of the cells to loose their viability (FIG. 1A). The HRTEC cells remained fully viable after 24 h incubation with up to 4 mg/ml of MAL. Monomeric α-lactalbumin had no effect on cell viability even at 10 mg/ml.

Figure 1B:
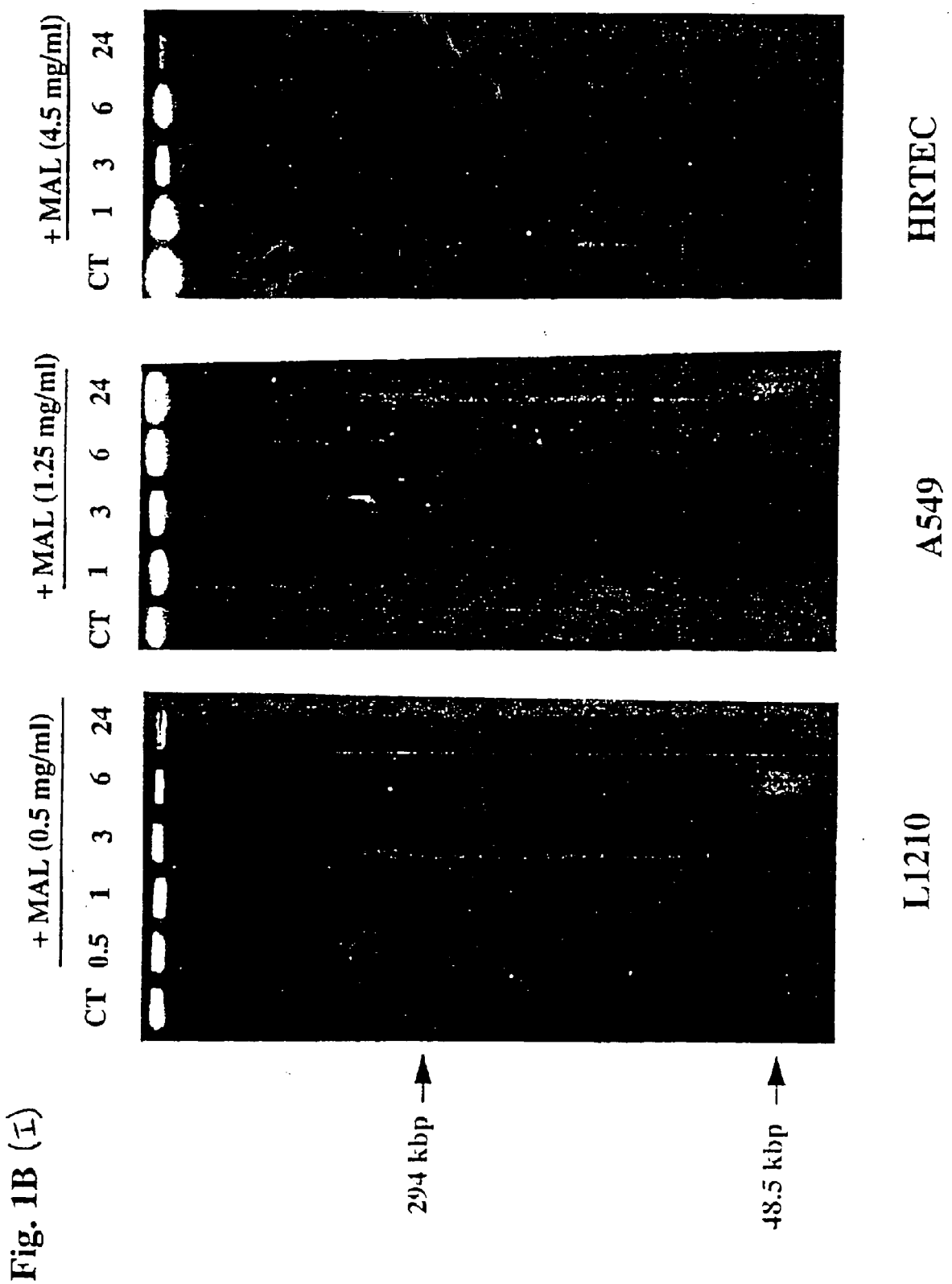
FIG. 1B shows the chromatin cleavage induced by MAL in these cells at various time points as measured by field inverse gel electrophoresis (panel I) and the oligonucleosome-length DNA fragmentation as analysed by conventional gel electrophoresis (panel II).

The kinetics of DNA fragmentation are illustrated in FIG. 1B. DNA fragmentation was highly time and concentration dependant. HMW DNA fragments were observed in the L1210 cells after 30 min incubation with MAL (0.5 mg/ml) and oligonucleosome length DNA fragments were detected after three hours. At lower MAL concentrations (0.3 mg/ml) fragmentation of DNA was first seen after 6 h and at higher concentrations of MAL (0.75 mg/ml) fragmentation was seen already at 2 h. At later times no fragmentation was seen due to secondary lysis of cells.

In the A549 cells HMW fragmentation was first detected after 6 h incubation with 1.0 mg/ml and was maximal at 1.5 mg/ml (FIG. 1B, panel 1). Further breakdown of DNA was observed with higher concentrations of MAL until finally no chromosomal DNA was seen (2.5 mg/ml). No oligonucleosomal fragmentation was detected (FIG. 1B, panel II).

The HRTEC cells did not undergo HMW DNA fragmentation after exposure to 4 mg/ml of MAL for 24 h (FIG. 1B).

These results demonstrated that differential sensitivity to MAL-induced apoptosis among the cell types studied. The L1210 cell line was highly sensitive, the A549 cells were intermediately sensitive and the non-transferred cultures were resistant to the effects of the protein complex within the tested concentration range. The monomeric form of the protein was inactive.

EXAMPLE 2

Cell Surface Binding of MAL Complexes

MAL, human α-lactalbumin (HLA) and immunoglobulin G were biotinylated according to the manufacturer's instructions or labelled with $^{125}$I with the lactoperoxidase method. Proteins were dissolved in PBSA-T buffer (30 mM Na$_2$HPO$_4$, 120 mM NaCl, pH 7.4, with 0.1% NaAzid, 0.05% Tween-20) and 25 μl of protein (25 μg) was incubated with 2 μl of $^{125}$(0.2 Ci), 2 μl of lactoperoxidase (2.5 mg/ml) and 2 μl of H$_2$O$_2$ (diluted 1:2000 in PBS) for 2 min at room temperature. The reaction was stopped by the addition of 500 μl of PBSA-T. The labelled protein was purified on a PD-10 column. 500 μl fractions in PBSA-T were eluted and fractions containing radioactivity were stored at 20° C. The labelled protein eluted in 1 ml of buffer and had an activity of approximately 2×10$^8$ cpm. L1210, A549 and HRTEC cells (3×10$^6$ cells/ml, 50 μl) were incubated in suspension with 50 μl of biotinylated MAL, ALA or BSA for various times at 37° C. The cells were washed with PBS by centrifugation at 320×g for 10 min and the supernatant was discarded. FITC-conjugated streptavidin (diluted 1:50 in PBS) was added and the cells were incubated for 30 min at room temperature. The cells were washed by centrifugation as above, suspended in 300 μl PBS and the surface fluorescence was analysed by flow cytometry on a Coulter Epics Profile II flow cytometer (Coulter Inc.), equipped with a 488 nm argon laser. Green fluorescence was detected with a 525 nm band pass filter. The PMT voltage was initially set to 1250 V and adjusted for day to day variation using calibration with Immunobeads (Coulter).

Cell surface bound material was examined by confocal microscopy, and quantitated by flow cytometry. Binding to the three cell types was detected after 10 min and reached a maximum after 30 min incubation, with a fluorescence intensity measured by flow cytometry that was 12.1, 13.4 and 8.5 times that of the streptavidin control. MAL was distributed in patches separated by unstained areas (FIG. 2A) seen on confocal microscopy.

Cell surface binding of MAL was also quantitated as the cell associated radioactivity during the first 30 min after addition of $^{125}$I-labelled MAL to the cells (FIG. 2B). Surface binding of radiolabelled protein to L1210, A549 or HRTEC cells in suspension (3×10$^6$ cells/ml, 100 μl) was quantitated in an Epics γ-counter (Coulter Inc.) after incubation with 1×10$^6$ cpm of $^{125}$I-labelled MAL, ALA or IgG for 30 min at 37° C. and the cells were washed three times by centrifugation at 320×g for 10 min with PBS.

Binding increased with the concentration of MAL, reaching saturation at 23 000, 20 000 and 18 000 cpm for L1210, A549 and HRTEC cells, respectively, after 30 min of exposure to 2×10$^6$ cpm compared to 1500 and 1300 cpm for L1210, and A549 cells of IgG. There was no difference in cell surface binding of MAL between the three cell types (FIG. 2B). Employing this method the binding of $-125^I$ labelled ALA was lower than that of MAL. After 30 minutes of exposure to 2×10$^6$ cpm of ALA binding was 5,000, 7,000 and 7,500 cpm for the L1210, A549 and HRTEC cells, respectively.

EXAMPLE 3

Nuclear Uptake of MAL

To detect intracellular protein, the cells were fixed at various times after addition of 0.3 mg/ml of biotinylated MAL for 5 min in phosphate-buffered paraformaldehyde (4%) (B. Sander et al., Immunol. Rev. (1991) 119: 65–92) at room temperature, washed in PBS, and permeabilized with 0.1% saponin in PBS. FITC conjugated streptavidin (diluted 1:100 in 0.1% saponin) was added and the cells were incubated for 30 min at room temperature. The cells were washed twice in PBS-saponin and once in PBS, mounted on a glass slide and analysed in a Bio-Rad 1024 laser scanning confocal equipment (Bio Rad Laboratories, Hemel-Hempstead, UK) attached to a Nikon Diaphot inverted microscope.

Permeabilization with the saponin allowed entry of streptavidin. Cells treated with medium, biotinylated BSA or α-lactalbumin served as controls (FIG. 3). Nuclear uptake of MAL was shown to occur rapidly in cells that were sensitive to its apoptosis-inducing effects. Nuclear staining of L1210 cells was first detected after about 2 hours in about 10% of the cells, and after 6 hours more than 70% of L1210 cell nuclei stained brightly. Cytoplasmic staining was not observed in those cells. Nuclear localisation of MAL in the A549 cells required longer incubation times (FIG. 3). About 15% of A549 cell nuclei stained brightly. In the meantime, MAL was observed in the cytoplasm of A549 cells as granular fluorescence evenly distributed throughout the cell. Nuclear uptake was not observed in the HRTEC cells exposed to the biotinylated MAL (1 mg/ml). There was a marked difference in the nuclear uptake of ALA compared to MAL. Nuclear staining of ALA was only detected in circa. 30% of L1210 cells after 6 hours and in about 15% OF A549 cells after 24 hours. No staining of ALA was detected in the HRTEC cells.

EXAMPLE 4

Radiolabelled Studies of Intracellular distribution

The intracellular distribution of MAL was further analysed in cells exposed to $^{125}$I-labelled MAL with $^{225}$I-labelled α-lactalbumin and IgG as controls (FIG. 4). Subcellular fractions were prepared after mechanic disruption of the cells and the amount of radiolabelled MAL in each fraction was determined in relation to the total cell-associated radioactivity measured prior to disruption of the cells. Fraction P1 contained mostly cell nuclei, P2 contained plasma-Golgi-, ER-membranes and mitochondria, P3 contained small vesicles and the supernatant. Fraction S contained the cytosolic proteins. The purity of the fractions was determined by quantitation of specific markers (DNA, alkaline phosphatase, RNA and catalase).

Specifically, cellular subfractionation was performed as described (J. Graham., Isolation of subcellular organelles and membranes., p161–1019. In D. Rickwood ed., Centrifugation, a practical approach, 2$^{nd}$ ed. IRL Press, Washington D.C.). L1210, A549 or HRTEC cells in suspension (3×10$^6$ cells/ml, 100 μla were incubated with 1×10$^6$ cpr of $^{125}$I-labelled MAL, ALA or IgG for various times at 37° C. The cells were washed three times with ice-cold PBS and the supernatants were discarded. The cells were suspended in 500 μl of homogenisation buffer (10 mM Tris-HCl, pH 7.8, 5 mM MgCl$_2$ and 2 mM CaCl$_2$ for L1210 cells and 0.15M NaCl, 2 mM EDTA, pH 7.5 for A549 cells), and homogenised by 50 strokes in a Dounce homogenizer (Thomas, Philadelphia, USA) with pestle size 415. Sucrose was added to a final concentration of 250 mm and the homogenate was centrifuged at 100×g for 25 min at RT. The first pellet contained nuclei, large mitochondria and large sheets of plasma membrane. The remaining supernatant was further centrifuged at 12 000×g for 30 min at 4° C. resulting in a second pellet containing mitochondria endoplasmic reticulum, plasma membrane and cytoplasmic organelles. The supernatant was finally centrifuged at 150,000×g for 2 h at 4° C. resulting in a pellet containing small vesicles, endoplasmic reticulum and a supernatant containing cytosolic proteins.

Specific cellular compartments were detected using enzymatic or chemical assays as described (Graham. supra. P.309–333).

DNA and RNA were detected in the fractions by the binding of ethidium bromide. Sample (1 vol) was mixed with 1 vol of heparin solution (25 μg/ml) and 1 ml of PBS or with 1 vol of heparin, 1 vol of RNAse A (50 μg/ml) and 1 vol of PBS. The samples were incubated at 37° C. for 20 min and 1 vol of ethidium bromide was added (25 μg/ml). Fluorescence was measured after 60 s incubation using an excitation wavelength of 360 nm and an emission wavelength of 580 nm. PBS served as blank, 1 vol of homogenate in 4 vol of PBS served as background correction factor and the fluorescence was compared to a DNA standard 25 μg/nl of λDNA).

Catalase activity was measured by mixing sample (0.5 ml) with $H_2O_2$ (0.5 ml), for 3 min at 4° C. $H_2SO_4$ (0.1 ml) was added to stop the reaction, $KMnO_4$ (0.7 ml) was added and the optical density of the sample was measured at 480 nm within 1 min.

Alkaline phophatase activity was detected by mixing 50 μl of sample with 200 μl of assay mixture (5 ml of 16 mM p-nitrophenylphosphate solution, 5 ml of 50 mM sodium borate buffer (pH 9.5) and 20 μl of 1 M $MgCl_2$) and incubated at 37° C. for 60 min. The absorbance was measured at 410 nm.

The distribution of $^{125}$I-labelled MAL and kinetics of uptake in the different cellular compartments, are shown in FIG. 4. As with biotinylated MAL, there were differences in nuclear localisation of $^{125}$I-labelled MAL, between the cell types. MAL accumulated in nuclei of L1210 cells with about 78% of the total radioactivity (34200/44000) recovered from the nuclear fraction (P1) after 6 h. MAL uptake into the nuclei of HRTEC cells was slow was slow with only 16% (2200/14000) of the total cell associated radioactivity in the nuclear fraction after 24 h of incubation. The A549 cells formed an intermediary group with about.52% of $^{125}$I-labelled MAL in the nuclear fraction (13700/27000) after 24 h. The total amount of cell-associated MAL in the other subcellular fractions did not differ to the same degree between the cell types. At the final time-point of measurement 4500 cpm (10%), 5100 cpm (195) and 2100 cpm (15%) were found in the pellet 2 from the L1210, A549 and HRTEC cells , respectively, and 800 cpm (2%), 1400 cpm (5%) and 1100 cpm (8%) were found in pellet 3 and 4500 cpm (10%), 6800 cpm (25%) and 8600 cpm (61%0 were found in the cytosolic fractions.

These results with biotinylated ALA were confirmed using $^{125}$I-labelled ALA. The monomeric protein entered the cells with lower efficiency than MAL, and was mainly recovered from the cytosol and not from the nuclei (FIG. 5). The nuclear uptake of $^{125}$I-labelled ALA in L1210, A549 and HRTEC cells was 23%, 27% and 37% of that observed for $^{125}$I-labelled MAL in the respective cell types. The cytoplasmic localisation of radiolabeled ALA was 80%, 75% and 60% of the amount measured for radiolabeled MAL.

The cellular localisation studies with biotinylated and $^{125}$I-labelled MAL suggested that MAL was transported into the nuclei and that the nuclear uptake of MAL into different cells was proportional to their sensitivity to MAL-induced apoptosis.

EXAMPLE 5

Effects of MAL Complexes on Isolated Nuclei

Nuclei were purified from L1210, A549 and HRTEC cells and incubated with low concentrations of MAL (0.2 and 0.4 mg/ml). The formation of HMW and oligonucleosome length DNA fragments was examined.

A549, L1210 and HRTEC nuclei were isolated from homogenised cells. Pellet 1 from the homogenisation was washed twice in nuclei buffer for 20 min at 100×g and suspended in nuclei buffer for experiments. Rat liver nuclei was isolated.

A549, L1210 or HRTEC nuclei in suspension were placed in individual wells in a 24-well plate (900 el), mixed with MAL, α-lactalbumin, lactoferrin or BSA (100 μl in nucleus buffer), incubated at 37° C. for 1 hour (L1210,) or 2 hours (A549 and HRTEC), harvested by aspiration, analysed for DNA fragmentation as described above. Inhibition of DNA fragmentation was studied by preincubating the nuclei for 10 min at RT with 0.5 mM EDTA, 10 μM BAPTA/AM, 10 μM verapamil, 1M VAD, 0.25 μM BOC, 0.5 μg/ml calpeptin, 0.5 μM DCI.

Active nuclear uptake was performed according to Adams et al. ((1990) supra.), with some modifications.

Briefly, 1×10$^6$ cells were incubated in 100 μl of nuclear transport buffer (NTB), with the addition of 1 μg/ml each of leupeptin, aprotinin, antipain, and 40 μg/ml of digitonin for 5 min at room temperature and washed by centrifugation at 320×g for 10 min in NTB. Biotinylated protein (5 μl, 5 mg/ml) was added to the cells in a total volume of 100 μl NTB supplemented with phosphcreatin, creatine phosphokinase and ATP, incubated for various time at RT and washed twice in NTB by centrifugation at 320×g for 10 min. The cells were treated with 0.2% Triton-X100 in NTB for 6 min and washed finally 1:100 dilution of fluorescein-conjugated strepatvidin was added for 30 min at RT and washed. The cells were then inspected by fluorescence microscopy in a Nikon Microphot (Japan) microscope or by laser scanning confocal microscopy in a BioRad MRC-1024 instrument.

A low degree of spontaneous DNA fragmentation occurred in unstimulated nuclei from the three cell types but MAL enhanced the formation of HMW DNA fragments after one hour and oligonucleosome length fragments after 2 hours (FIG. 6).

Digitonin permeabilizes the plasma nembrane, but leaves the nuclear membrane intact. L1210, A549 and HRTEC cells were permeabilized with digitonin in nuclear transport buffer, washed and exposed to biotinylated MAL in buffer supplemented with phosphocreatin, creatin phosphokinase and ATP. Human IgG and monomeric α-lactalbumin were used as controls. MAL was taken directly into the nuclei of digitonin treated cells with maximum levels reached after 20 min (FIG. 7e).

When adding 0.4 mg/ml of MAL to digitoninpermeabilized cells, HMW DNA fragments were formed after 1 hour and oligonucleosomal fragments after 2 hours. ALA entered nuclei of digitonin-permabilzed cells as predicted by its molecular mass (14 kDa) and produced bright staining of the nuclei (FIG. 7c). IgG was not detected in isolated nuclei or in nuclei of digitonin-permabilized cells (FIG. 7a).

These experiments demonstrated that both ALA and MAL was transported into the nuclei, but that only MAL could induce DNA fragmentation in isolated nuclei, apparently in the absence of activated cytoplasm. There was however, no difference in sensitivity to MAL-induced DNA fragmentation between nuclei from the three cell types. This suggested that the differential sensitivity to MAL was determined by the nuclear targeting process rather than by the effect on the nuclei per se.

EXAMPLE 6

Role of the Nuclear Pore Complex for the Nuclear Uptake of MAL

The role of active transport over the nuclear pore was examined in digitonin-treated cells, using wheat-germ agglutinin (WGA) which binds to the nucleoporins and inhibits the transport of importin-protein complex through the nuclear pore. The digitonin-permeabilized L1210 cells were preincubated with 50 µg/ml of WGA for 20 minutes, washed and exposed to biotinylated MAL. IgG and α-lactalbumin were used as controls (FIG. 7).

Specifically, before adding biotinylated protein, cells were preincubated with 50 µg/ml of wheat-germ agglutinin (WGA), 0.5 mM EDTA, 0.5 mM BAPTA/AM or 10 µM verapamil for 20 min at RT. The cells pretreated with WGA were then washed by centrifugation in NTB at 320×g for 10 min before addition of protein.

The integrity of the nuclear membrane was tested by adding sera containing anti-nuclear antibodies to digitonin- and Triton-X100 permeabilized cells followed by incubation with anti-human IgG antibodies (1:100) for 30 min at RT, washing by centrifugation at 320×g for 10 min and visualisation as described above. Permeabilization with Triton-X 100 resulted in bright nuclear staining whereas no detectable staining was observed in the digitonin-permeabilized cells at a concentration of 40 µg/ml of digitonin. (The antibodies were kindly provided by the Clinical Immunology Laboratory, Lund). WGA completely blocked the nuclear uptake of MAL, suggesting that transport was via the nuclear pore complex (FIG. 7f). Human IgG was not taken up in the presence or absence of WGA (FIGS. 7a and 7b). Monomeric α-lactalbumin is a 14 kDa protein that diffuses freely over the nuclear membrane. WGA had no effect on the uptake of α-lactalbumin into the nuclei of digitonin-treated cells (FIG. 7d). Wheat germ agglutin was also used to inhibti DNA fragmentaton in isolated nuclei and digitonin-permeabilized cells. Preincubation with 50 µg/ml of WGA partially blocked the DNA fragmentation from exposure to 0.4 mg/ml of MAL (FIG. 6)

EXAMPLE 7

Role of $Ca^{2+}$ for Nuclear Uptake of MAL and for the Induction of DNA Fragmentation The MAL induced apoptosis was previously shown to require extracellular $Ca^{2+}$. This suggested that $Ca^{2+}$ might influence the nuclear uptake mechanism and or the induction of DNA fragmentation once MAL reaches the cell nuclei. L1210, A549 and HRTEC cells were pretreated with inhibitors of $Ca^{2+}$ uptake (verapamil and nefidipine), with extracellular $Ca^{2+}$ chelators (EDTA and EGTA) and with an intracellular $Ca^{2+}$ chelator (BAPTA/AM). $^{125}$I-labelled MAL was added to the cells, and the nuclear uptake was examined after 6 hours in L1210 cells and after 24 hours in A549 and HRTEC cells. The $Ca^{2+}$ uptake inhibitors and chelators had no effect on the nuclear uptake of MAL (FIG. 8). The MAL induced DNA fragmentation was subsequently examined in control nuclei and nuclei incubated with $Ca^{2+}$ inhibitors. Verapamil, EDTA and BAPTA/AM completely blocked the DNA fragmentation in L1210 and A549 nuclei. These results demonstrated that DNA fragmentation by MAL required $Ca^{2+}$, but that the nuclear uptake of MAL was $Ca^{2+1}$ independent.

What is claimed is:

1. A method for delivering a reagent into the nucleoplasm of a cell, for the purpose of killing said cell or for diagnosis of cancer, wherein said cell is susceptible to being killed by an oligomeric form of α-lactalbumin (MAL), said method comprising combining said reagent with MAL to form a complex, and applying said complex to the cell, wherein said complex is delivered into the nucleoplasm of the cell.

2. A method according to claim 1, wherein the cell is a tumour cell.

3. A method according to claim 1, wherein the reagent is an agent capable of killing cells.

4. A method according to claim 3, wherein said reagent is a cytotoxin.

5. A method according to claim 4, wherein the cytotoxin is selected from the group consisting of a chemotherapeutic reagent, a microbial toxin and a monoclonal antibody.

6. A method according to claim 1, wherein the reagent is a diagnostic reagent.

7. A method according to claim 6, wherein said reagent comprises a labeling agent.

8. A method according to claim 7, wherein the labeling agent is selected from the group consisting of biotin and a radioactive label.

9. A method according to claim 8, wherein the labeling agent is a radioactive label selected from the group consisting of 125I, 14C and 35S.

10. A method according to claim 1, wherein the reagent is coupled to MAL by conjugation.

11. A method according to claim 1, wherein said reagent is coupled to MAL by covalent bonding.

12. A method according to claim 1, wherein the said reagent is covalently bonded to MAL by way of a linking or spacer group.

13. A method according to claim 1, wherein said reagent comprises a polypeptide or protein, wherein said polypeptide or protein is fused to MAL.

14. A method of diagnosing cancer in a patient comprising administering to a patient an effective amount of a protein complex comprising an oligomeric form of α-lactalbumin (MAL) and a labeling agent, and detecting said labeling agent in the nucleus of a cell.

15. A method of diagnosing cancer comprising applying to cells which are suspected of being cancerous an effective amount of a protein complex comprising an oligomeric form of α-lactalbumin (MAL) and a labeling agent, and observing penetration of said agent into the nucleus of the cells, wherein penetration into the nucleus is indicative of cancer.

16. A method according to claim 15, wherein said method is carried out in vitro on a sample removed from a patient.

17. A method of detecting a cancer cell comprising applying to a cell which is suspected of being cancerous, a protein complex comprising an oligomeric form of α-lactalbumin (MAL) and a labeling agent, and observing penetration of said complex into the nucleus of the cell, wherein penetration into the nucleus is indicative of a cancer cell.

18. A method of detecting a reagent in a nucleoplasm of a cell, wherein said cell is susceptible to being killed by an olipomeric form of α-lactalbumin (MAL), said method comprising applying to said cell an effective amount of a protein complex comprising an oligomeric form of t-lactalbumin (MAL) and said reagent, allowing penetration of said protein complex into the nucleus of the cell and detecting said reagent in the nucleus of said cell.

19. A method according to claim 18, wherein the cell is a tumour cell.

20. A method according to claim 18, wherein the reagent is an agent capable of killing cells.

21. A method according to claim 20, wherein said reagent is a cytotoxin.

22. A method according to claim 21, wherein the cytotoxin is selected from the group consisting of a chemotherapeutic reagent, a microbial toxin and a monoclonal antibody.

23. A method according to claim 18, wherein the reagent is a diagnostic reagent.

24. A method according to claim 23, wherein said reagent comprises a labeling agent.

25. A method according to claim 24, wherein the labeling agent is selected from the group consisting of biotin and a radioactive label.

26. A method according to claim 25, wherein the labeling agent is a radioactive label selected from the group consisting of 125I, 14C and 35S.

27. A method according to claim 18, wherein the reagent is coupled to MAL by conjugation.

28. A method according to claim 19, wherein said reagent is coupled to MAL by covalent bonding.

29. A method according to claim 19, wherein the said reagent is covalently bonded to MAL by way of a linking or spacer group.

30. A method according to claim 18, wherein said reagent comprises a polypeptide or protein, wherein said polypeptide or protein is fused to MAL.

* * * * *